United States Patent [19]

Rothfuss et al.

[11] 4,026,520
[45] May 31, 1977

[54] SURGICAL STAPLE EXTRACTOR

[75] Inventors: Robert G. Rothfuss, Bellevue, Ky.;
Russell C. Stone, Cincinnati, Ohio;
Matthew H. Wykoff, Bridgewater, N.J.

[73] Assignee: Senco Products, Inc., Cincinnati, Ohio

[22] Filed: Mar. 5, 1976

[21] Appl. No.: 664,231

[52] U.S. Cl. .............................................. 254/28
[51] Int. Cl.² ........................................ B25C 11/00
[58] Field of Search .................... 254/28; 227/63

[56] References Cited

UNITED STATES PATENTS

| | | | |
|---|---|---|---|
| 2,202,984 | 6/1940 | Drypolcher | 254/28 |
| 2,400,988 | 5/1946 | Goessel | 254/28 |
| 2,762,604 | 9/1956 | Misson | 254/28 |

*Primary Examiner*—Al Lawrence Smith
*Assistant Examiner*—Robert C. Watson
*Attorney, Agent, or Firm*—Melville, Strasser, Foster & Hoffman

[57] ABSTRACT

A manually operated surgical staple extractor comprising a pliers-like tool having first and second handle elements pivotally joined together and swingable between open and closed positions. The first handle element terminates at its forward end in a pair of elongated anvils in parallel spaced relationship. The forward ends of the anvils are angled toward each with their front-most tips substantially contiguous. The rearward ends of said anvils are provided with aligned notches, the first handle element providing a steep upwardly and rearwardly sloping surface adjacent each of the notches. The second handle element is operatively connected to a thin blade means shorter than the anvils. When the first and second handle elements are in their open position, the lower edge of the blade means lies above the anvils. When the handle elements are shifted to their closed position, the blade is pivoted downwardly such that its lower edge passes between the anvils to a position therebelow. The blade means is sufficiently thin that, as it passes between the anvils, there is clearance between the blade means and each anvil substantially equal to the diameter of the crown portion of a staple.

16 Claims, 10 Drawing Figures

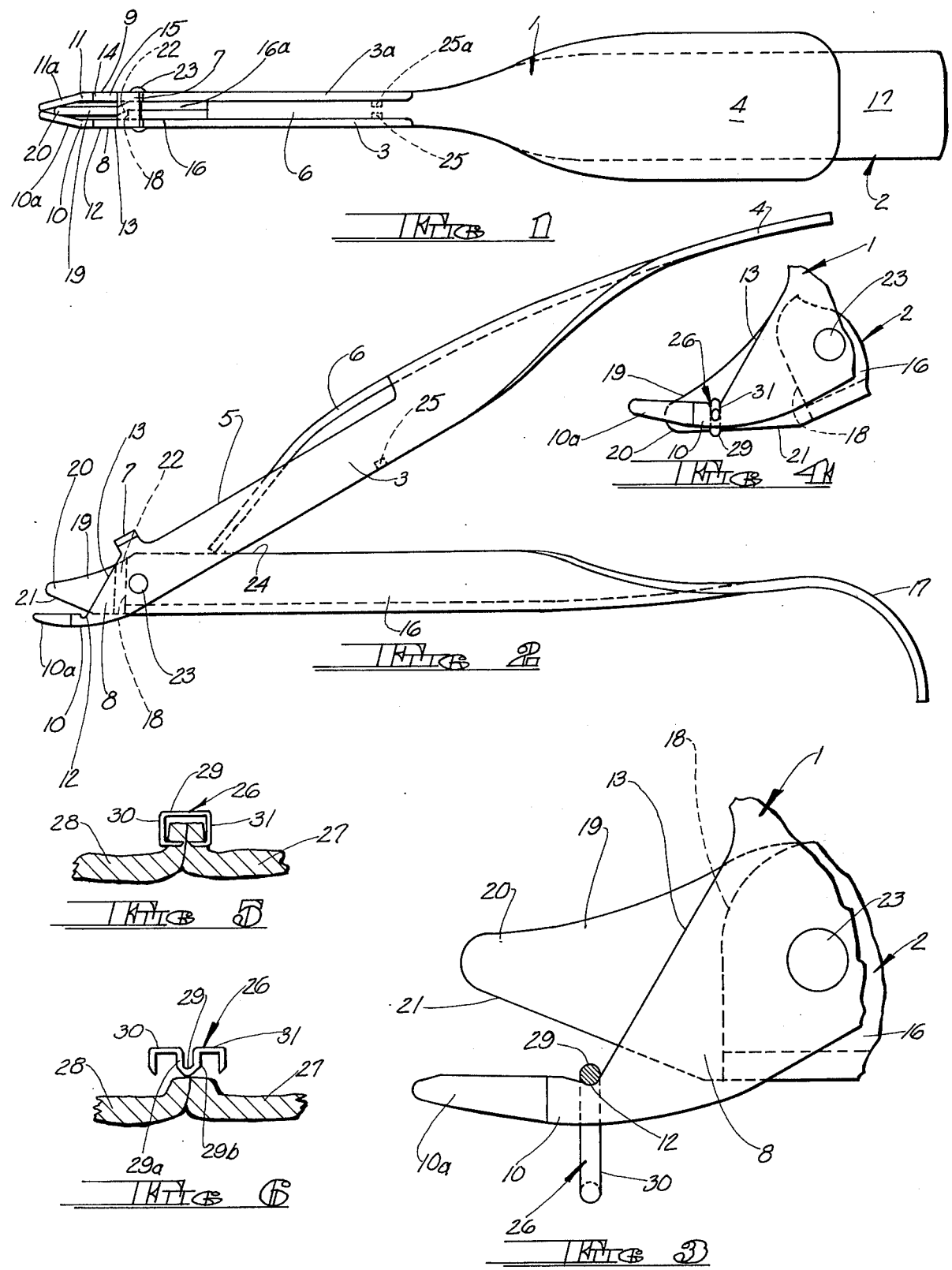

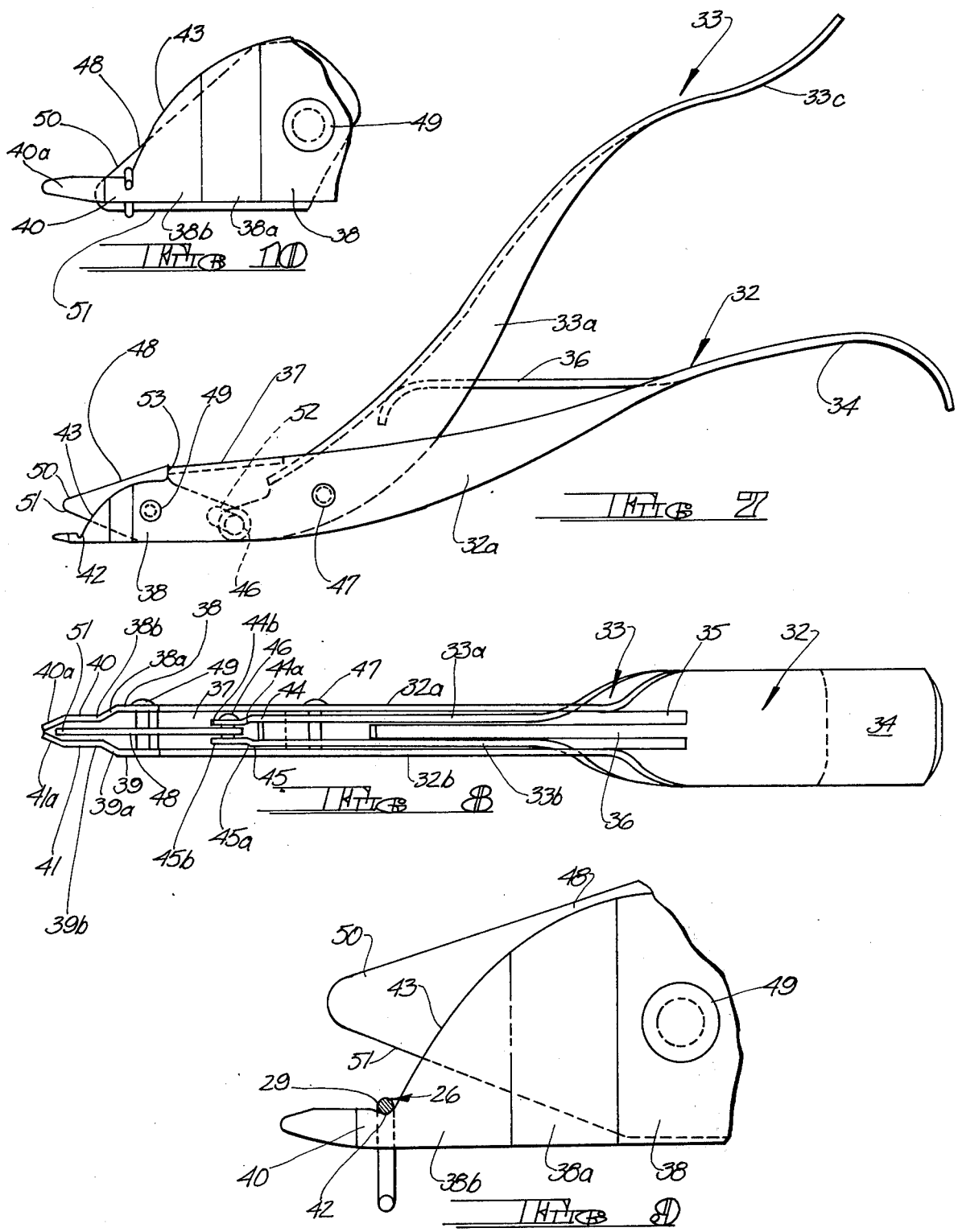

SURGICAL STAPLE EXTRACTOR

BACKGROUND OF THE INVENTION

1. Field of the Invention

The invention relates to a staple extractor, and more particularly to a manually operated extractor for surgical staples.

2. Description of the Prior Art

In recent years surgeons have turned more and more to the use of surgical staples, rather than conventional thread sutures, for closing wounds or incisions in the skin of a patient. This is true because the stapling operation is often times simpler. More importantly, however, is the fact that the stapling operation is very much faster than conventional thread suturing. Thus, particularly in those instances where a considerable amount of suturing is required, the length of time for the suturing operation and the length of time the patient must be maintained under anesthesia are greatly reduced when surgical staples are used.

A typical type of surgical staple is illustrated in U.S. Pat. No. 3,643,851; 3,717,294 and 3,837,555. A staple of the type shown in these patents initially has an elongated crown terminating in downwardly depending portions. The free ends of the downwardly depending portions are provided with downwardly and outwardly sloping cuts, forming points. During the forming and implanting of such a staple in the skin of a patient, end portions of the elongated crown are bent downwardly. This forms a staple with a narrower crown and L-shaped legs, the pointed ends of which are opposed.

Another type of surgical staple is taught in the copending application Ser. No. 585,804, filed June 11, 1975 in the name of Robert G. Rothfuss and entitled SURGICAL STAPLE. This staple initially comprises a central crown portion terminating at either end in portions sloping upwardly and outwardly, these upwardly and outwardly sloping portions, in turn, terminate in downwardly and outwardly sloping portions. The last mentioned portions are provided with cut surfaces forming points. These cut surfaces initially lie in a position substantially perpendicular to the staple crown and the skin of the patient to be joined. During forming and implanting of this type of staple, the upwardly and outwardly sloping portions of the staple, at their juncture with the crown, are bent downwardly to form a staple having a crown and L-shaped legs, the points of which are opposed.

Either type of staple described above may be removed from the skin of a patient by bending the staple crown into a U-shaped configuration. This will cause the L-shaped legs of the staple to shift upwardly and outwardly so that they may be lifted from the patient's skin.

Prior art workers have developed manual extractors for bending the crown of surgical staples and lifting the staple from the patients skin. In its typical form, a prior art extractor comprises a pliers-like tool having first and second handle means pivoted together and formed of sheet metal. The first handle means terminates in a pair of anvils in parallel spaced relationship. The anvils are provided at their rearward ends with notches so that, when the anvils are slipped under the crown portion of a surgical staple, the crown will be received in the notches.

The second handle of the extractor generally is provided with a relatively thick, two-ply, blade-like forward end substantially as long or longer than the anvils. When the handle elements of the extractor are in their open position, this blade lies above the anvils and the notches therein. As the handle elements are shifted to their closed position, the blade element passes between the anvils and the notches therein making the above described U-shaped bend in the staple crown located in the notches.

It will be understood that when the anvils are slipped beneath the crown of a staple, they will rub against traumatized areas of the skin, causing pain to the patient. Since the blade is as long or longer than the anvils, it partially obscures the anvils, making their proper insertion under the staple crown and location of the staple crown in the anvil notches more difficult. Furthermore, when the extractor anvils are parallel throughout their length, the operator may inadvertently slip only one anvil under the crown of the staple to be extracted. Under these circumstances the staple will not properly open and if the operator pulls the extractor upwardly the patient will undergo severe pain.

When the typical prior art extractor is actuated to bend the crown, clearance between the blade and the anvils is such that the crown tends to make the anvils spread apart, further irritating the traumatized skin. As a further consequence, the legs of the U-shaped bend in the staple crown are generally non-parallel, with the result that the staple legs themselves are not fully opened. In addition, prior art extractors are generally constructed in such a way that the first handle element can inadvertently become "flipped" (or pivoted through more than 180°) with respect to the second handle element, thus rendering the extractor useless until its handle elements are returned to their proper orientation. Finally, prior art extractors are generally provided with means to bias the handle elements to their open position. This biasing means can become dislocated, tending to jam the extractor.

The extractor of the present invention is intended to overcome these problems encountered with prior art extractors. The extractor of the present invention is simple in construction and inexpensive to manufacture either as a single-use, disposable tool or as a sterilizable and reusuable tool. The extractor of the present invention will be described in two-piece and three-piece embodiments.

SUMMARY OF THE INVENTION

The manually operated surgical staple extractor of the present invention is in the form of a pliers-like tool having first and second handle elements pivotally joined together near their forward ends. These handle elements are manually shiftable between open and closed positions and may be biased to their open position.

The first handle element is bifurcated at its forward end, the bifurcations terminating in a pair of elongated anvils in parallel spaced relationship. The forward ends of the anvils are angled toward each other with the front-most tips thereof being contiguous or nearly so. At their rearward ends, the anvils are provided with aligned notches to receive the crown of a staple. The bifurcations of the first handle element provide a steep upwardly and rearwardly sloping surface adjacent each of the anvil notches to assist in and assure the location of a staple crown in the notches.

A thin blade means is located between the bifurcations of the first handle element and is operatively connected to the forward end of the second anvil element. The blade means has a nose portion shorter than the anvils and a lower edge adapted to produce a U-shaped bend in the crown of a staple located in the anvil notches. The blade nose portion is shiftable by the second handle element between a first position (when the handle elements are in their open position) wherein the lower edge of the nose lies above the anvils and the notches therein and a second position (when the handle elements are in their closed position) wherein the nose lies between the anvils with the lower edge of the nose located below the anvils. The anvils are so spaced from each other and the nose of the blade means is sufficiently thin that clearance is provided between the nose and each anvil at least substantially equal to the diameter of the crown of the staple being bent. This minimizes spreading or shifting of the anvils during the staple extracting process and enables the legs of the U-shape bend formed in the staple crown to be substantially parallel, fully opening the staple legs and rendering removal of the staple less painful.

In one embodiment, the extractor of the present invention comprises a two-piece tool held together with an appropriate pivot pin, the blade comprising an integral, one-piece part of the second handle element. In another embodiment, the extractor of the present invention comprises a three-piece tool. In this instance, the blade is a separate element affixed between the bifurcations of the first handle element and operatively connected to the forward end of the second handle element. This allows that part of the extractor in contact with the skin of the patient to remain stationary. This, in turn, minimizes extraneous movement of the extractor anvils during the staple extraction helping to minimize the major cause of pain to the patient.

Both embodiments of the extractor of the present invention lend themselves well to manufacture as a single use, disposable tool or as a re-sterilizable, reusuable tool.

BRIEF DESCRIPTION OF THE DRAWINGS

FIG. 1 is a top view of the extractor of the present invention.

FIG. 2 is a side elevational view of the extractor of FIG. 1.

FIG. 3 is an enlarged fragmentary elevational view of the extractor of FIG. 2 illustrating the relative positions of the anvils and blade prior to the bending of the staple crown.

FIG. 4 is an enlarged fragmentary elevational view similar to FIG. 3 illustrating the relative positions of the anvils and blade after the bending of the staple crown.

FIG. 5 is a fragmentary elevational view, partly in cross section, showing a staple embedded in the skin of a patient.

FIG. 6 is a fragmentary elevational view, partly in cross-section, illustrating the configuration of the staple after extraction.

FIG. 7 is a side elevational view of another embodiment of the extractor of the present invention.

FIG. 8 is a bottom view of the extractor of FIG. 7.

FIG. 9 is an enlarged fragmentary elevational view illustrating the relative positions of the blade and anvils of the extractor of FIGS. 7 and 8 prior to the bending of the staple crown.

FIG. 10 is a fragmentary elevational view, similar to FIG. 9, and showing the relative positions of the blade and anvils after the bending of the staple crown.

DESCRIPTION OF THE PREFERRED EMBODIMENTS

The extractor tool of the present invention is best illustrated in FIGS. 1 and 2. The extractor comprises a first handle element generally indicated at 1 and a second handle element generally indicated at 2. The first handle element 1 is a unitary, one-piece structure folded so as to have an inverted U-shaped cross section, with downwardly depending legs 3 and 3a, except at its rearward end which terminates in a broad portion 4 to be engaged by the operator's thumb.

An elongated U-shaped opening 5 is made in the handle element 1 prior to its forming into the above noted U-shaped cross section, so as to provide a resilient tine 6 the purpose of which will be described hereinafter.

Forwardly of opening 5 a portion of the base of the inverted U-shaped cross section remains forming a bridge 7. The legs 3 and 3a continue forwardly to provide bifurcations 8 and 9 terminating in elongated anvils 10 and 11. It will be apparent from FIG. 1 that bifurcations 8 and 9 and anvils 10 and 11 are in parallel spaced relationship with the forwardmost ends 10a and 11a of anvils 10 and 11 being angled toward each other with their forwardmost tips being contiguous or nearly so. At the juncture of bifurcation 8 and anvil 10, a notch 12 is provided. That portion of bifurcation 8 adjacent notch 12 is configured to present a steep, upwardly and rearwardly sloping surface 13. In similar fashion, a notch 14 is located at the juncture of bifurcation 9 and anvil 11, the bifurcation 9 providing a steep upwardly and rearwardly sloping surface 15 equivalent to surface 13 of bifurcation 8.

The second handle element 2 also comprises an integral, one-piece structure the central portion of which is folded into a U-shaped cross section with upwardly extending legs 16 and 16a in parallel abutting relationship (see FIG. 1). Near the rearward end of handle element 2 the legs 16a and 16b flare outwardly to form the wide, hook-shape portion 17 to be engaged by the middle and fourth fingers of the hand of the operator.

At the forward end of handle element 2, leg 16 terminates as at 18 (see FIGS. 1, 2 and 3). Leg 16a, on the other hand, is extended to form a blade 19 having nose portion 20 and lower bending edge 21. As is evident from FIG. 1, the continuation of leg 16a is offset as at 22 so that the blade 19 extends centrally of the legs 16 and 16a of the handle element 2. In this way, a single thickness blade is provided.

By virtue of the fact that legs 16 and 16a of handle element 2 are abuting, while legs 3 and 3a of handle element 1 are in parallel spaced relationship, the central portion of handle element 2 can be received between the legs 3 and 3a of handle element 1. Handle elements 1 and 2 are pivotally joined together by pivot pin or rivet 23 near their forward ends.

As will be evident from FIG. 2, the upstanding legs 16 and 16a of handle element 2 provide a surface 24 along which the resilient tine 6 of handle element 1 can exert pressure. Resilient tine 16 serves to bias handle elements 1 and 2 to their open position, as illustrated in FIGS. 1 and 2. The surface 24 of handle element 2 in cooperation with legs 3 and 3a of handle element 1 form a trough-like structure for the free end of tine 6, assuring that the tine cannot become laterally dislocated to jam handle elements 1 and 2. The legs 3 and 3a of handle element 1 may be provided with integral tabs 25 and 25a, respectively, which cooperate with surface 24 to determine the relative closed position of handle elements 1 and 2.

To better understand the operation of the extractor of FIGS. 1 through 4, reference is first made to FIG. 5. In FIG. 5 a surgical staple (generally indicated at 26) is shown in its fully formed and implanted condition joining skin segments 27 and 28. It will be noted that the fully formed staple 26 has a crown portion 29 and a pair of L-shaped legs 30 and 31 in opposed position.

The handle elements 1 and 2 of the extractor of the present invention may be grasped by the operator in any convenient fashion. Normally, the operator's thumb will engage the portion 4 of handle element 1 and the operator's middle finger and fourth finger will hook beneath the portion 17 of handle element 2. The first step in the use of the extractor is to insert anvils 10 and 11 beneath the crown 29 of staple 26 until the crown 29 is located in aligned notches 12 and 14 of anvils 10 and 11. This is shown in FIG. 3. As is evident from FIGS. 1 and 3, anvils 10 and 11 and their forward portions 10a and 11a are elongated, of thin gauge (as viewed in plan in FIG. 1) and narrow (as viewed in side elevation in FIG. 3). The nose portion 20 of blade 19, being shorter than the anvils 10 and 11, permits the operator to clearly observe the anvils 10 and 11 and the staple 26 during this step. The fact that anvil tips 10a and 11a are contiguous, or substanially so, enables them to be moe easily inserted beneath staple crown 29, and precludes the possibility of only one anvil being inserted under the staple crown 29. The steep upward and rearward bifurcation surfaces 13 and 15 serve as stops, assuring that staple crown 29 is properly located in aligned notches 12 and 14. All of these factors materially reduce the pain experienced by the patient during this initial step.

At this point, handle elements 1 and 2 are shifted to their closed position forcing the blade 19 against staple crown 29 and downwardly between anvils 10 and 11. As is shown in FIG. 4, this operation produces a U-shaped bend in the crown 29 of staple 26, most clearly illustrated in FIG. 6. As is evident from FIG. 6, this bending of crown 29 causes legs 30 and 31 to shift upwardly and outwardly, enabling the staple 26 to be pulled upwardly and away from skin segments 27 and 28.

As will be noted in FIG. 1, the single thickness blade 19 is free to pass between anvils 10 and 11 with clearance on both sides of blade 19 at the positions of notches 12 and 14 at least substantially equal to the diameter of crown 29 of staple 26. This clearance provides a number of advantages. First of all, the bend in staple crown 29 can be formed with minimal or no spreading of anvils 10 and 11 and their tips 10a and 11a. This, of course, eliminates a possible source of pain to the patient. In addition, the U-shaped bend in crown 29 (as illustrated in FIG. 6) can be formed with substantially parallel upstanding legs 29a and 29b, assuring that staple legs 30 and 31 will be fully opened and allowing stapel 26 to be lifted from skin segments 27 and 28 with minimal pain. Furthermore, the staple 26 can be readily released from the extractor by simply permitting handle elements 1 and 2 to return to their open position (as shown in FIG. 2) under the influence of resilient tine 6.

As indicated above, the inwardly bent anvil tips 10a and 11a facilitate the lining up of the extractor with staple 26 during insertion of the anvils 10 and 11 beneath the staple crown 29. The fact that the anvils 10 and 11 and their tips 10a and 11a are narrow, as viewed in FIG. 3, minimizes trauma in placing them beneath staple crown 29. Since blade 19 comprises a single thickness of the material from which handle element 2 is made, the above described sharper U-shaped bend in staple crown 29 can be made, even in small staples of minimum crown length.

The bridge 7, most clearly shown in FIGS. 1 and 2, serves a number of purposes. First of all, it assures the proper spacing between the blade 19 and anvils 10 and 11. Furthermore, the bridge renders the structure stronger. Finally, the bridge cooperates with the blade 19, serving as a stop to determine the maximum amount of which handle element 1 can be rotated about rivet 23 with respect to handle element 2 beyond the normal open position of handle elements 1 and 2 illustrated in FIG. 2. This prevents handle element 1 from being inadvertently flipped to a position wherein it underlies handle element 2 rendering the extractor useless until the proper orientation of handle elements 1 and 2 is regained.

The extractor of FIGS. 1 and 2 is of simple two-piece construction, handle elements 1 and 2 being joined together by rivet or pivot pin 23. This structure can be inexpensively manufactured from non-corrosive sheet metal or other material of sufficient strength, compatible with a surgical environment and capable of sterilization. Rivet 23 may also be made of a non-corrosive metal or the like. Thus, the extractor may be readily made as a single-use, disposable tool lending itself to pre-sterile packaging. On the other hand, the extractor may be made of stainless steel or the like, if it is intended to be a reusable tool.

A second embodiment of the extractor of the present invention is illustrated in FIGS. 7 through 10. In this embodiment, the extractor is again provided with two handle elements generally indicated at 32 and 33. Handle element 32 is formed of non-corrosive sheet metal or the like and length wise is of a gentle S-curve configuration. Handle element 32 is formed into an inverted U-shaped configuration (providing downwardly depending legs 32a and 32b) except at its rearward end where the handle is provided with a broad, hook-shaped portion 34 adapted to be engaged by the operator's middle and fourth fingers.

The upper surface of handle element 32 has an elongated U-shaped opening 35 therein, forming an integral, resilient tine 36, the purpose of which will be described hereinafter. The remaining top portion of the handle, ahead of opening 35, forms a bridge 37 joining the downwardly depending legs 32a and 32b.

At their forwardmost ends, legs 32a and 32b are extended to form parallel bifurcations 38 and 39. These bifurcations are bent inwardly as at 38a and 39a and terminate in parallel portions 38b and 39b which lie closer together. Portions 38b and 39b terminate in parallel anvils 40 and 41. Anvils 40 and 41, in turn, are provided with tips 40a and 41a which are bent inwardly so that their forwardmost ends are contiguous or nearly so. Anvils 40 and 41 and their respective tips 40a and 41a are narrow in height and thin in gauge for the same reasons described with respect to anvils 10 and 11 and their respective tips 10a and 11a of the embodiment illustrated in FIGS. 1 through 4. Anvils 40 and 41 are provided with aligned notches equivalent to the notches 12 and 14 of FIGS. 1 through 4. One such notch in anvil 40 is shown at 42 in FIGS. 7 and 9. The notches in anvils 40 and 41 serve the same purpose as notches 12 and 14 of the embodiment of FIGS. 1 through 4. The notches of anvils 40 and 41 are followed by steep upwardly and rearwardly sloping surfaces equivalent to the surfaces 13 and 15 of FIGS. 1 and 2. These surfaces are located on bifurcation portions 38b and 39b, the surface on bifurcation portion 38b being shown at 43 in FIGS. 7, 9 and 10.

Handle element 33 is also configured longitudinally in a gentle S-shape. Handle element 33 is formed of non-corrosive sheet metal or the like so as to have an inverted U-shaped cross section with downwardly depending legs 33a and 33b in parallel spaced relationship. At their forward ends, legs 33a and 33b are extended to form bifurcations 44 and 45 having inwardly bent portions 44a and 45a terminating in parallel portions 44b and 45b. The bifurcation portions 44b and 45b are provided with coaxial perforations adapted to receive a rivet or pivot pin 46 of non-corrosive metal or the like. The purpose of rivet 46 will be described hereinafter. The forward end of handle element 33 extends through opening 35 in the upper portion of handle element 32 and lies between legs 32a and 32b of handle element 32, being pivotally affixed thereto by a pivot pin or rivet 47 of non-corrosive metal or the like. The rearward end of handle element 33 is flattened as at 33c.

The embodiment of FIGS. 7 through 10 utilizes a third element in the form of a blade 48 made of single thickness, non-corrosive metal or the like. Blade 48 is pivotally mounted between bifurcations 38 and 39 of handle element 32 by pivot pin or rivet 49, made of non-corrosive metal or the like.

Blade 48 has a forward nose portion 50, shorter than anvil tips 40a and 41a and provided with a lower bending edge 51. The other end of blade 48 has an enlarged or elongated opening 52 therein adapted to receive the previously described rivet or pivot pin 46. In this way, blade 48 is operatively connected to bifurcation portions 44b and 45b of handle element 33.

FIG. 7 illustrates this embodiment of the extractor of the present invention in its normal condition with handle elements 32 and 33 in their open position. The handle elements 32 and 33 are biased to their open position by the engagement of resilient tine 36 on the underside of handle element 33. It will be evident from FIG. 7 that the openmost position of handle elements 32 and 33 is determined by the abutment of shoulder portion 53 of blade 48 against the forward edge of bridge 37 of handle element 32. When handle elements 32 and 33 are shifted to their closed position, against the action of resilient tein 36, the connection of handle element 33 and blade 48 via rivet or pivot pin 46 will cause blade 48 to pivot about rivet or pivot pin 49 in a counter clockwise direction (as viewed in FIG. 7) to a position wherein the blade nose 50 passes between anvils 40 and 41 with the bending edge 51 of the blade 48 extending therebelow (see FIG. 10). Upon release of handle elements 32 and 33, the extractor parts will return to their respective normal positions illustrated in FIG. 7. It will be appreciated that the interaction of handle element 33 and blade 48 is permitted by virtue of elongated hole 52. While hole 52 in blade 48 is illustrated as being elongated, it will be understood by one skilled in the art that the same purpose could be served if hole 52 where of circular configuration and had a diameter sufficiently greater than the diameter of rivet or pivot pin 46.

In use, the staple extractor embodiment of FIGS. 7 through 10 is grasped by the operator in any convenient manner. For example, the operator's middle and fourth fingers may engage about the hook-shaped portion 34 of handle element 32 with the operators thumb engaging flat portion 33c of handle element 33. The anvils 40 and 41 are first slipped beneath the staple in the same manner described with respect to the embodiment of FIGS. 1 through 3. Again, the fact that anvil tips 40a and 41a are substantially contiguous; the fact that the anvils 40 and 41 and their tips 40a and 41a are elongated, narrow in height and of thin gauge; and the fact that nose 50 of blade 48 is shorter than anvils 40 and 41 and their tips 40a and 41a, all work together to facilitate the lining up of the extractor with the staple and the placement of both anvils 40 and 41 beneath the staple crown with a minimum of pain to the patient. Again, the step upwardly and rearwardly angled edges of bifurcation portions 38b and 39b (one such edge shown at 43 in FIG. 9) assures that staple crown 29 will be properly located in the aligned anvil notches (one of which is shown at 42 in FIGS. 7 and 9).

After this first stage of the extracting process, handle elements 32 and 33 may be shifted to their closed position causing blade 48 to assume the position illustrated in FIG. 10. This forms the above described U-shaped bend in staple crown 29, as illustrated in FIG. 5. The clearance between blade 48 and anvils 40 and 41 is again at least substantially equal to the diameter of staple crown 29 (see FIG. 8), assuring that the legs 29a and 29b of the U-shaped bend in staple crown 29 will again be parallel (see FIG. 5), with staple legs 30 and 31 in their fully opened position. This is true even when the extractor is used to remove a staple having a minimum size crown.

At this point, the staple may be lifted from the skin of a patient with minimal pain. In the embodiment of FIGS. 7 and 10, the bridge 37 of handle element 32 will insure the precise spacing between blade 48 and anvils 40 and 41 and will render the extractor assembly stronger.

The clearance provided between blade 48 and anvils 40 and 41 will minimize spreading of anvils 40 and 41 and their tips 40a and 41a during the extracting process. This, in turn, eliminates a major source of pain to the patient. This same clearance also permits an extracted staple to be readily dropped from the extractor upon release of handle elements 32 and 33 to their normal, open position.

The three-piece design of the embodiment of FIGS. 7 through 10 allows handle element 32 and its anvils 40 and 41 and their tips 40a and 41a to remain stationary while in contact with the skin of the patient. Only blade 48 closes down to bend staple crown 29. This feature minimizes extraneous movement of the extractor anvils during the staple extraction, helping to eliminate a major source of pain. The mechanical connection between handle 33 and blade 48 prevents handle 33 from being inadvertently flipped with respect to handle 32.

As with the embodiment of FIGS. 1 through 3, the extractor of FIGS. 7 through 10 may be made of any suitable material of sufficent strength, capable of sterilization and compatible with a surgical environment. When intended to be a single-use, disposable instrument, the extractor may be made, for example, of a non-corrosive metal, as indicated above. The extractor lends itself well to disposable, pre-sterile packaging.

When intended for reuse and resterilization, it may be made of stainless steel or the like.

Modifications may be made in the invention without departing from the spirit of it.

The embodiments of the invention in which an exclusive property or privilege is claimed are defined as follows:

1. A manually operated extractor for a surgical staple of the type having, when implanted in the skin of a patient, an exposed crown and opposed L-shaped skin engaging legs, said extractor comprising a pliers-like tool having first and second handle elements pivotally joined together near their forward ends and being shiftable between an open position and a closed position, said first handle element having a bifurcated forward end, said bifurcations terminating in a pair of elongated anvils in parallel spaced relationship and adapted to be slipped beneath said crown portion of a surgical staple in the skin of a patient, said anvils having forward ends angled toward each other with the frontmost tips thereof being substantially contiguous, said anvils having rearward ends provided with aligned notches to receive said crown of a surgical staple, said bifurcations providing a steep upwardly and rearwardly sloping surface adjacent each of said notches to assist in locating said staple crown in said notches, a thin blade means being located between said bifurcations of said first handle element, said second handle element being operatively connected at its forward end to said blade means, said blade means having a nose portion shorter than said anvils and having a lower edge, said blade nose portion being shiftable by said second handle element between a first position when said handle elements are in said open position wherein said lower edge of said nose lies above said anvils and said notches therein and a second position when said handle elements are in said closed position wherein said nose lies between said anvils with said lower edge below said anvils, there being clearance between said nose portion and each of said anvils at least substantially equal to the diameter of said crown portion of said staple, whereby when said anvils are slipped beneath the crown portion of a staple in the skin of a patient with the crown located in said aligned anvil notches and said blade is shifted to its second position by said second handle element, said crown of said staple will be formed into a U-shape causing said L-shaped staple legs to shift upwardly and outwardly enabling them to be lifted from the skin of a patient.

2. The structure claimed in claim 1 including means to bias said handle elements to their open position.

3. The structure claimed in claim 1 wherein said blade means comprises an integral one-piece part of said second handle element.

4. The structure claimed in claim 1 wherein said blade means comprises a separate element pivotally attached to said first handle element between said bifurcations thereof, said blade element having a forward end comprising said nose and a rearward end operatively connected to said forward end of said second handle element.

5. The structure claimed in claim 3 including means to bias said handle elements to their open position.

6. The structure claimed in claim 3 wherein said first handle element comprises an elongated one-piece member folded transversely so as to have an inverted U-shaped cross section with downwardly depending legs in parallel spaced relationship, said legs of said first handle element being extended at said forward end of said first handle element to form said bifurcations, said legs flairing outwardly at the other end of said first handle element to form a broad portion for engagement by the hand of the operator, said second handle element comprising an elongated one-piece member folded transversely so as to have a U-shaped cross section, with upwardly extending legs in parallel abutting relationship, one of said legs being extended at said forward end of said second handle element to form said blade means, said legs of said second handle element flairing outwardly at the other end of said second handle element to form a broad portion to be engaged by the hand of the operator, said second handle element lying below said first handle element with said upstanding legs of said second handle element being receivable between said downwardly depending legs of said first handle element and said blade means extending between said bifurcations, said legs of second handle element adjacent said blade being pivotally affixed to and between said legs of said first handle element adjacent said bifurcations by a pivot pin.

7. The structure claimed in claim 4 wherein said first handle element comprises an elongated one-piece member folded transversely so as to have an inverted U-shaped cross section with downwardly depending legs in parallel spaced relationship, said legs of said first handle element being extended at said forward end of said first handle element to form said bifurcations, said legs flairing outwardly at the other end of said first handle element to form a broad portion for engagement by the hand of the operator, said second handle element comprising an elongated one-piece member folded transversely so as to have an inverted U-shaped cross section with downwardly depending legs in parallel spaced relationship said legs at said forward end of said second handle element being extended to form a second pair of bifurcations, said legs flairing outwardly at the other end of said second handle element to form a broad portion for engagement by the hand of the operator, said first handle element having an elongated opening formed therein between the legs thereof, said second handle element lying above said first handle element with said forward end of said second handle element extending through said opening in said first handle element and being pivotally attached to and between said legs of said first handle element by a pivot pin, said blade means being pivotally attached to and between said bifurcations of said first handle element by a pivot pin, said rearward end of said blade means having an elongated slot therein, said rearward end of said blade means lying between and being operatively connected to said bifurcations of said second handle element by a pivot pin passing through coaxial holes in said last mention bifurcations and said slot in said rearward end of said blade means.

8. The structure claimed in claim 6 wherein said first and second handle elements are formed from non-corrosive sheet metal.

9. The structure claimed in claim 6 including an integral resilient tine on said first handle element extending downwardly and forwardly between said legs thereof, said upstanding legs of said second handle element providing an upper surface to be engaged by said tine whereby said tine urges said first and second handle elements to their open position.

10. The structure claimed in claim 6 wherein that portion of said inverted U-shaped cross section of said first handle element at said forward end thereof and joining said downwardly depending legs thereof comprises a bridge maintaining said bifurcations of said first handle element and said blade in proper alignment and cooperating with said blade means to determine the open-most position of said first and second handle elements.

11. The structure claimed in claim 7 wherein said first and second handle elements and said blade means are formed from non-corrosive sheet metal, said blade means being a single thickness of said sheet metal.

12. The structure claimed in claim 7 including an integral resilient tine extending upwardly and forwardly of said first handle element from a point near said broad portion thereof, said tine engaging said second handle element between said legs thereof whereby said tine urges said first and second handle elements to their open position.

13. The structure claimed in claim 7 wherein that portion of said inverted U-shaped cross section of said first handle element at said forward end thereof and joining said downwardly depending legs thereof comprises a bridge maintaining said bifurcations of said first handle element and said blade in proper alignment and cooperating with said blade means to determine the open-most position of said first and second handle elements.

14. The structure claimed in claim 8 wherein said sheet metal is stainless steel, said extractor comprising said sheet metal is stainless steel, said extractor comprising a reusable and resterilizable tool.

15. The structure claimed in claim 9 including integral, inturned, opposed tabs on said downwardly depending legs of said first handle element adapted to contact said surface to be engaged by said tine to determine said closed position of said first and second handle elements.

16. The structure claimed in claim 11 wherein said sheet metal is stainless steel, said extractor comprising a reusable and resterilizable tool.

* * * * *